United States Patent
Lall

(10) Patent No.: US 8,374,691 B2
(45) Date of Patent: Feb. 12, 2013

(54) METHODS AND SYSTEMS FOR DETERMINING IF AN ARRHYTHMIA INITIATED IN AN ATRIUM OR A VENTRICLE

(75) Inventor: Carolyn Lall, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 164 days.

(21) Appl. No.: 12/987,487

(22) Filed: Jan. 10, 2011

(65) Prior Publication Data

US 2012/0179220 A1 Jul. 12, 2012

(51) Int. Cl.
 *A61N 1/365* (2006.01)
(52) U.S. Cl. .............................. 607/14; 607/17; 600/510
(58) Field of Classification Search .................. 600/510, 600/518; 607/4, 14, 17–18
See application file for complete search history.

(56) References Cited

U.S. PATENT DOCUMENTS

| | | |
|---|---|---|
| 4,295,474 A | 10/1981 | Fischell |
| 4,686,988 A | 8/1987 | Sholder |
| 4,708,142 A | 11/1987 | DeCote, Jr. |
| 4,712,555 A | 12/1987 | Thornander et al. |
| 4,729,376 A | 3/1988 | DeCote, Jr. |
| 4,788,980 A | 12/1988 | Mann et al. |
| 4,809,697 A | 3/1989 | Causey, III et al. |
| 4,940,052 A | 7/1990 | Mann et al. |
| 4,944,298 A | 7/1990 | Sholder |
| 4,944,299 A | 7/1990 | Silvian |
| 4,969,467 A | 11/1990 | Callaghan et al. |
| 5,240,009 A | 8/1993 | Williams |
| 5,350,410 A | 9/1994 | Kleks et al. |
| 5,462,060 A | 10/1995 | Jacobson et al. |
| 5,732,708 A | 3/1998 | Nau et al. |
| 5,779,645 A | 7/1998 | Olson et al. |
| 5,868,793 A | 2/1999 | Nitzsche et al. |
| 6,275,734 B1 | 8/2001 | McClure et al. |
| 6,636,764 B1 | 10/2003 | Fain et al. |
| 7,065,402 B2 | 6/2006 | Henry et al. |
| 2012/0029586 A1* | 2/2012 | Kumar et al. ................... 607/14 |

OTHER PUBLICATIONS

Mletzko, Ralph et al., "Enhanded Specificity of a Dual Chamber ICD Arrhythmia Detection Algorithm by Rate Stability Criteria," PACE. 2004;27:1113-1119.
Sadoul, Nicolas et al., "Incidence and Clinical Relevance of Slow Ventricular Tachycardia in Implantable Cardioverter-Defibrillator Recipients—An International Multicenter Prospective Study," Circulation. 2005;112;946-953.
Sadoul, Nicolas MD et al, "Diagnostic Performance of a Dual-Chamber Cardioverter Defibrillator Programmed with Nominal Settings: A European Prospective Study," J Cardiovasc Electrophysiol. Jan. 2002;13:25-32.
Schimpf, R. MD et al., "Algorithms for Better Arrhythmia Discrimination in Implantable Cardioverter Defibrillators," Curr Cardiol Rep. 2001;3(6):467-472.
Stoppler, C, "Rhythm classification used in defibrillator-therapy: The PARAD/PARAD+ (TM) algorithm implemented into the implantable Cardioverter/Defibrillator defender IV DR," Herzschrittmacher. 2000;20(3):215-229.

* cited by examiner

*Primary Examiner* — Rex R Holmes

(57) ABSTRACT

Validated atrial and/or ventricular interval decreases are used to discriminate between VT and SVT. Atrial and/or ventricular intervals are monitored in order to detect decreases in such intervals (which are indicative in increases in rate). The atrial intervals can be, e.g., AA intervals, and the ventricular intervals can be, e.g., VV intervals. A detected atrial and/or ventricular interval decrease can be a decrease that is greater than an interval decrease threshold. Detected atrial and/or ventricular interval decreases can be validated by examining atrial and/or ventricular intervals before and after a detected atrial and/or ventricular interval decrease. The use of the validated atrial and/or ventricular interval decreases to classify an arrhythmia as SVT or VT can be called arrhythmia initiation analysis, since it is believed to determine whether the initiation of the arrhythmia is in an atrium or a ventricle.

21 Claims, 5 Drawing Sheets

METHODS AND SYSTEMS FOR DETERMINING IF AN ARRHYTHMIA INITIATED IN AN ATRIUM OR A VENTRICLE

FIELD OF THE INVENTION

Embodiments of the present invention relate to implantable cardiac devices and methods for use therewith, that are used to discriminate between different types of arrhythmias.

BACKGROUND

In a normal heart, cells of the sinoatrial node (SA node) spontaneously depolarize and thereby initiate an action potential. This action potential propagates rapidly through the atria (which contract), slowly through the atrioventricular node (AV node), the atrioventricular bundle (AV bundle or His bundle) and then to the ventricles, which causes ventricular contraction. This sequence of events is known as normal sinus rhythm (NSR). Thus, in a normal heart, ventricular rhythm relies on conduction of action potentials through the AV node and AV bundle.

Rhythms that do not follow the sequence of events described above are known as arrhythmias. Those that result in a heart rate slower than normal are known as bradyarrhythmias; those that result in a faster heart rate than normal are called tachyarrhythmias. Tachyarrhythmias are further classified as supraventricular tachyarrhythmias (SVTs) and ventricular tachyarrhythmia (VT). Supraventricular tachyarrhythmias (SVTs) are characterized by abnormal rhythms that may arise in the atria or the atrioventricular node (AV node). For example, a paroxysmal SVT can exhibit heart rates between approximately 140 beats per minute (bpm) and approximately 250 bpm. However, the most common SVTs are typically atrial flutter (AFL) and atrial fibrillation (AF). In addition, many SVTs involve the AV node, for example, AV nodal reentry tachycardia (AVNRT) where an electrical loop or circuit includes the AV node.

Atrial flutter (AFL) can result when an early beat triggers a "circus circular current" that travels in regular cycles around the atrium, pushing the atrial rate up to approximately 250 bpm to approximately 350 bpm. The atrioventricular node between the atria and ventricles will often block one of every two beats, keeping the ventricular rate at about 125 bpm to about 175 bpm. This is the pulse rate that will be felt, even though the atria are beating more rapidly. At this pace, the ventricles will usually continue to pump blood relatively effectively for many hours or even days. A patient with underlying heart disease, however, may experience chest pain, faintness, or even heart failure as a result of the continuing increased stress on the heart muscle. In some individuals, the ventricular rate may also be slower if there is increased block of impulses in the AV node, or faster if there is little or no block.

If the cardiac impulse fails to follow a regular circuit and divides along multiple pathways, a chaos of uncoordinated beats results, producing atrial fibrillation (AF). AF commonly occurs when the atrium is enlarged (usually because of heart disease). In addition, it can occur in the absence of any apparent heart disease. In AF, the atrial rate can increase to more than 350 bpm and cause the atria to fail to pump blood effectively. Under such circumstances, the ventricular beat may also become haphazard, producing a rapid irregular pulse. Although AF may cause the heart to lose approximately 20 to 30 percent of its pumping effectiveness, the volume of blood pumped by the ventricles usually remains within the margin of safety, again because the atrioventricular node blocks out many of the chaotic beats. Hence, during AF, the ventricles may contract at a lesser rate than the atria, for example, of approximately 125 bpm to approximately 175 bpm.

Overall, SVTs are not typically immediately life threatening when compared to ventricular arrhythmias, examples of which are discussed below.

Ventricular arrhythmias, which originate in the ventricles, include ventricular tachycardia (VT) and ventricular fibrillation (VF). Ventricular arrhythmias are often associated with rapid and/or chaotic ventricular rhythms. For example, sustained ventricular tachycardia can lead to ventricular fibrillation. In sustained ventricular tachycardia, consecutive impulses arise from the ventricles at a rate of 100 bpm or more. Such activity may degenerate further into disorganized electrical activity known as ventricular fibrillation (VF). In VF, disorganized action potentials can cause the myocardium to quiver rather than contract. Such chaotic quivering can greatly reduce the heart's pumping ability. Indeed, approximately two-thirds of all deaths from arrhythmia are caused by VF. A variety of conditions such as, but not limited to, hypoxia, ischemia, pharmacologic therapy (e.g., sympathomimetics), and asynchronous pacing may promote onset of ventricular arrhythmia.

It has been common practice for an implantable cardioverter defibrillator (ICD) to monitor heart rate, or more commonly the ventricular rate, of a patient and classify the cardiac condition of the patient based on this heart rate. For example, a tachyarrhythmia may be defined as any rate in a range above a designated threshold. This range is then divided into ventricular tachycardia and ventricular fibrillation zones. The ventricular tachycardia zone may be further divided into slow ventricular tachycardia and fast ventricular tachycardia zones.

As described above, SVTs and ventricular arrhythmias may lead to ventricular rates in excess of 100 bpm. In other words, ventricular rates of SVTs can overlap with rates of tachycardias of ventricular origin. These SVTs are often well tolerated and require no intervention. Further, physically active patients can have heart rates during exercise that overlap with their tachycardia rates. Accordingly, discrimination of VT from SVT, including increased heart rates due to exercise, may require more than just knowledge of a patient's ventricular rate. In other words, using heart rate as the sole criterion to classify the cardiac condition of a patient is often not sufficient.

To improve the specificity and accuracy of arrhythmia characterization, many implantable cardiac devices (ICDs) can also examine the morphology of an intracardiac electrogram (IEGM), in addition to the heart rate. The shape of an intracardiac complex can include information on the origin and sequence of the heart's electrical activity. A normal intracardiac complex traverses the AV node and is conducted by specialized cardiac tissue throughout the ventricles. This results in a distinctive complex morphology. A tachycardia of ventricular origin often has a different morphology due to its ectopic origin and conductance through cardiac muscle tissue. As such, in addition to monitoring heart rate, some ICDs are capable of performing morphology discrimination to classify the cardiac condition of the patient. For example, a template based on the morphology of a "known" signal can be stored in the ICD. The "known" signal can be, for example, a signal collected during a period where a patient is known to exhibit a normal sinus rhythm. By comparing the morphology characteristics (e.g., number, amplitude, sequence and/or polarity of waveform peaks, as well as the area of the peaks) of an arrhythmia to the template, the ICD can calculate the match (or lack thereof) between the waveforms. For a further description of morphology discrimination, refer to U.S. Pat. No. 5,240,009 (Williams), entitled "Medical Device with Morphology Discrimination" and to U.S. Pat. No. 5,779,645 (Olson et al.) entitled "System and Method for Waveform Morphology Comparison," which patents are hereby incorporated by reference. These are just a few examples of morphology discriminator algorithms and parameters, which are not intended to be limiting.

Sudden onset and interval stability (also know as rate stability), are examples of other factors that can be monitored to improve the specificity of arrhythmia characterization. Also, the relationship between ventricular rate (V) and atrial rate (A) can be used to characterize an arrhythmia. For example, this can be part of a rate branch algorithm, which, depending on V and A, may follow one of three branches: a V<A rate branch; a V=A (within a specified tolerance) rate branch; and a V>A rate branch. If V<A, then morphology discrimination and/or interval stability may be available to distinguish VT from AF or AFL. If A and V are essentially the same (within a certain tolerance), then morphology discrimination and/or sudden onset may be available to distinguish VT from sinus tachycardia. If V>A, then an arrhythmia may be characterized as VT. Also, specific branches can be turned on or off. For example, if V is greater than the tachycardia threshold but essentially the same as A, and the V=A branch is turned off, then the algorithm can cause the V>A branch to be followed, and the arrhythmia may be classified as VT. Additional details of an exemplary rate branch algorithm are provided in U.S. Pat. No. 6,636,764 (Fain et al.), entitled "Safety Backup in Arrhythmia Discrimination Algorithm," which is incorporated herein by reference. Also, atrioventricular association (AVA) can also be used to distinguish AFL from VT. In an exemplary AVA algorithm, the AV interval is measured from each ventricular sensed event to its preceding atrial event and an AVA Delta is then calculated as the difference between the second longest AV interval and the second shortest AV interval in a recent group of intervals. If the measured AVA Delta is less than a programmable AVA threshold parameter, the AV intervals are considered stable, which is indicative of SVT. If the measured AVA Delta is greater than or equal to a programmable AVA threshold parameter, the AV intervals are considered unstable, which is indicative of VT. More generally, the relative rate of the atria and ventricles and/or the timing relationship between atrial and ventricular events can be considered.

Typically an ICD is programmed to provide a therapy in response to an arrhythmia being detected, where the type of therapy corresponds to the type of arrhythmia that the ICD believes it has detected. For example, VT may be treated with a therapy consisting of low-energy pacing pulses designed to capture the ventricles. This therapy is referred to as ventricular Anti-Tachycardia Pacing therapy (ATP). VT may also be treated with relatively low energy, synchronized cardioversion shocks. VF, on the other hand, is typically treated more aggressively with high energy shocks. SVT may not be treated, or may be treated using atrial ATP or atrial defibrillation. Quite often, SVT is treated using medication, or ablation.

Inappropriate therapy is a huge problem for ICD patients. Inappropriate therapies, specifically inappropriate shocks cause great suffering among the ICD patient population. Patients receive a potentially life-saving device (the ICD) only to find out that it sometimes malfunctions and inflicts both pain and harm without any warning whatsoever. For a secondary prevention patient, this might be bearable since he or she has experienced and been saved from a lethal tachyarrhythmia in the past. For the primary prevention patient, however, without a history of arrhythmias who receives the ICD only based on a risk score, this is more difficult to bear.

Today only a few of the patients who are candidates for an ICD receive one. This is mostly an economic issue; although several studies indicate that an ICD is a cost effective treatment in indicated patients. However, if the performance of the devices improves, the willingness to put in an ICD, especially in young primary prevention patients, will increase.

Despite the numerous arrhythmia discrimination techniques that exist, examples of which were provided above, delivery of inappropriate shocks remains a major problem with ICDs today. A common cause of inappropriate shocks in ICD devices are atrial arrhythmias that are conducted to the ventricles at a high rate. Accordingly, there is still a need for new, and preferably improved, arrhythmia discrimination techniques.

SUMMARY

Embodiments of the present invention are directed to techniques for use with implantable cardiac devices to discriminate between ventricular tachyarrhythmia (VT) and supraventricular tachyarrhythmia (SVT). Embodiments of the present invention are also directed to implantable cardiac devices and systems that are configured to implement such techniques.

Described herein is a new arrhythmia discrimination algorithm that identifies the chamber in which the arrhythmia initiated and uses this information to classify the arrhythmia as either VT or SVT. In one embodiment, the algorithm analyzes the atrial and ventricular rates to identify a significant rate increase (interval decrease) in each chamber. It classifies the arrhythmia as SVT or VT based on which chamber's rate increased (interval decreased) first. If the atrial rate increased first, the atrium is driving the arrhythmia and thus the arrhythmia is classified as a SVT. If the ventricular rate increased first, the ventricle is driving the arrhythmia and thus the arrhythmia is classified as a VT. If neither rate increased significantly, the arrhythmia is classified as a Sinus Tachycardia (which is a type of SVT).

In accordance with specific embodiments, validated atrial and/or ventricular interval decreases are used to discriminate between VT and SVT. Atrial and/or ventricular intervals are monitored in order to detect decreases in such intervals. Each interval can be, e.g., the interval between two intrinsic events, the interval between two paced events or the interval between an intrinsic event and a paced event. A detected atrial and/or ventricular interval decrease can be a decrease that is greater than an interval decrease threshold. Detected atrial and/or ventricular interval decreases can be validated by examining atrial and/or ventricular intervals before and after a detected atrial and/or ventricular interval decrease. The use of the validated atrial and/or ventricular interval decreases to classify an arrhythmia as a SVT or VT can be called arrhythmia initiation analysis since it is believed to determine whether the initiation of an arrhythmia is in an atrium or a ventricle.

In an embodiment, any atrial interval decrease that is greater than an atrial interval decrease threshold is detected for a pair of consecutive atrial intervals within a window of time. If such an atrial interval decrease is detected, it is determined whether the detected atrial interval decrease is valid based on atrial intervals before and after the detected atrial interval decrease.

In an embodiment, any ventricular interval decrease that is greater than a ventricular interval decrease threshold is detected for a pair of consecutive ventricular intervals within the window. If such a ventricular interval decrease is detected, it is determined whether the detected ventricular interval decrease is valid based on ventricular intervals before and after the detected ventricular interval decrease.

Discrimination between VT and SVT is then performed based on any determined valid atrial interval decrease and/or valid ventricular interval decrease.

This summary is not intended to be a complete description of the invention. Other features and advantages of the invention will appear from the following description in which the preferred embodiments have been set forth in detail, in conjunction with the accompanying drawings and claims.

DETAILED DESCRIPTION OF PREFERRED EMBODIMENTS

The following description includes a best mode presently contemplated for the device. This description is not to be taken in a limiting sense but is made merely for the purpose of describing the general principles of the device. In the description that follows, like numerals or reference designators will be used to refer to like parts or elements throughout.

The disclosed systems and methods, which are for use in discriminating between different types of arrhythmias, are generally intended for use with an implantable cardiac device capable of detecting and treating arrhythmias. An exemplary implantable cardiac device will thus be described in conjunction with FIGS. 1 and 2, in which embodiments of the present invention described herein could be implemented. It is recognized, however, that numerous variations of such a device exist in which the methods could be implemented.

Figure 1:
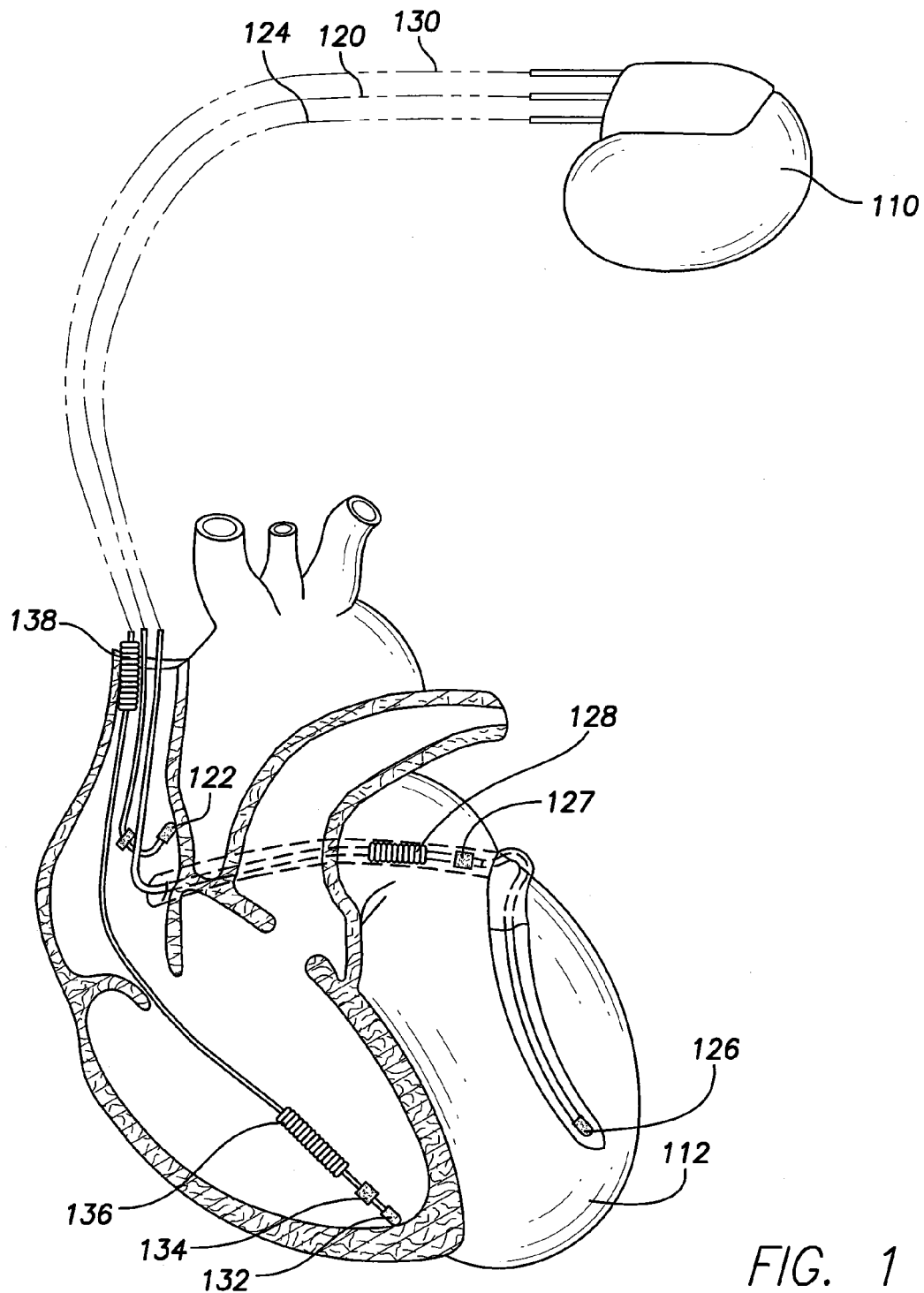
FIG. 1 is a simplified, partly cutaway view illustrating an implantable stimulation device in electrical communication with at least three leads implanted into a patient's heart for delivering multi-chamber stimulation and shock therapy.

Referring to FIG. 1, an exemplary implantable device 110 (also referred to as a pacing device, a pacing apparatus, a cardiac stimulation device, or simply a device) is in electrical communication with a patient's heart 112 by way of three leads, 120, 124 and 130, suitable for delivering multi-chamber stimulation. Preferably, the exemplary device 110 is also capable of delivering shock therapy.

To sense atrial cardiac signals and to provide right atrial chamber stimulation therapy, the stimulation device 110 is coupled to an implantable right atrial lead 120 having at least an atrial tip electrode 122, which typically is implanted in the patient's right atrial appendage. To sense left atrial and ventricular cardiac signals and to provide left-chamber pacing therapy, the stimulation device 110 is coupled to a "coronary sinus" lead 124 designed for placement in the "coronary sinus region" via the coronary sinus for positioning a distal electrode adjacent to the left ventricular and/or additional electrode(s) adjacent to the left atrium. As used herein, the phrase "coronary sinus region" refers to the vasculature of the left ventricular, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 124 is designed to receive left atrial and ventricular cardiac signals and to deliver left atrial and ventricular pacing therapy using at least a left ventricular tip electrode 126, left atrial pacing therapy using at least a left atrial ring electrode 127, and shocking therapy using at least a left atrial coil electrode 128. The present invention may of course be practiced with a coronary sinus lead that does not include left atrial sensing, pacing or shocking electrodes.

The stimulation device 110 is also shown in electrical communication with the patient's heart 112 by way of an implantable right ventricular lead 130 having, in this embodiment, a right ventricular tip electrode 132, a right ventricular ring electrode 134, a right ventricular (RV) coil electrode 136, and an SVC coil electrode 138. Typically, the right ventricular lead 130 is transvenously inserted into the heart 112 so as to place the right ventricular tip electrode 132 in the right ventricular apex so that the RV coil electrode 136 will be positioned in the right ventricular and the SVC coil electrode 138 will be positioned in the superior vena cava. Accordingly, the right ventricular lead 130 is capable of receiving cardiac signals and delivering stimulation in the form of pacing and shock therapy to the right ventricular. It will be understood by those skilled in the art that other lead and electrode configurations such as epicardial leads and electrodes may be used in practicing the invention.

Figure 2:
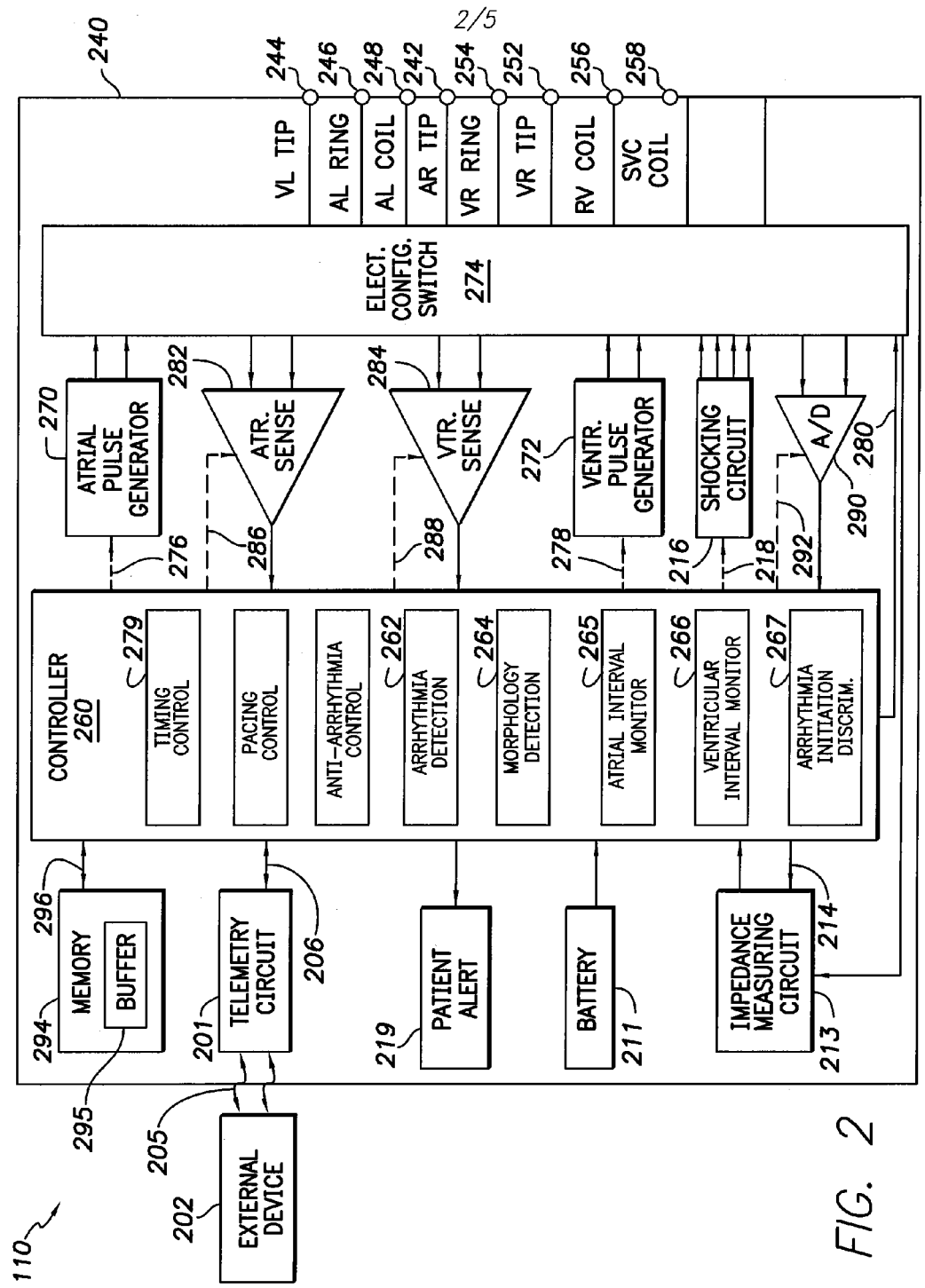
FIG. 2 is a functional block diagram of the multi-chamber implantable stimulation device of FIG. 1, illustrating the basic elements that provide pacing stimulation, cardioversion, and defibrillation in four chambers of the heart.

As illustrated in FIG. 2, a simplified block diagram is shown of the multi-chamber implantable device 110, which is capable of treating both fast and slow arrhythmias with stimulation therapy, including pacing, cardioversion and defibrillation stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with pacing, cardioversion and defibrillation stimulation.

The housing 240 for the implantable device 110, shown schematically in FIG. 2, is often referred to as the "can", "case" or "case electrode" and may be programmably selected to act as the return electrode for all "unipolar" modes. The housing 240 may further be used as a return electrode alone or in combination with one or more of the coil electrodes, 128, 136 and 138, for shocking purposes. The housing 240 further includes a connector (not shown) having a plurality of terminals, 242, 244, 246, 248, 252, 254, 256, and 258 (shown schematically and, for convenience, the names of the electrodes to which they are connected are shown next to the terminals). As such, to achieve right atrial sensing and pacing, the connector includes at least a right atrial tip terminal ($A_R$ TIP) 242 adapted for connection to the atrial tip electrode 122.

To achieve left atrial and ventricular sensing, pacing and shocking, the connector includes at least a left ventricular tip terminal ($V_L$ TIP) 244, a left atrial ring terminal ($A_L$ RING) 246, and a left atrial shocking terminal ($A_L$ COIL) 248, which are adapted for connection to the left ventricular ring electrode 126, the left atrial tip electrode 127, and the left atrial coil electrode 128, respectively.

To support right ventricular sensing, pacing and shocking, the connector further includes a right ventricular tip terminal ($V_R$ TIP) 252, a right ventricular ring terminal ($V_R$ RING) 254, a right ventricular shocking terminal (Rv COIL) 256, and an SVC shocking terminal (SVC COIL) 258, which are adapted for connection to the right ventricular tip electrode 132, right ventricular ring electrode 134, the RV coil electrode 136, and the SVC coil electrode 138, respectively.

At the core of the implantable device 110 is a programmable microcontroller 260 which controls the various types and modes of stimulation therapy. As is well known in the art, the microcontroller 260 typically includes a microprocessor, or equivalent control circuitry, designed specifically for controlling the delivery of stimulation therapy and can further include RAM or ROM memory, logic and timing circuitry, state machine circuitry, and I/O circuitry. Typically, the microcontroller 260 includes the ability to process or monitor input signals (data) as controlled by a program code stored in a designated block of memory. The details of the design of the microcontroller 260 are not critical to the present invention. Rather, any suitable microcontroller 260 can be used to carry out the functions described herein. The use of microprocessor-based control circuits for performing timing and data analysis functions are well known in the art. In specific embodiments of the present invention, the microcontroller 260 performs some or all of the steps associated with arrhythmia detection and myocardial ischemia detection.

Representative types of control circuitry that may be used with the invention include the microprocessor-based control system of U.S. Pat. No. 4,940,052 (Mann et. al.), entitled "Microprocessor Controlled Rate-Responsive Pacemaker Having Automatic Rate Response Threshold Adjustment" and the state-machines of U.S. Pat. No. 4,712,555 (Thornander et al.), entitled "Physiologically Responsive Pacemaker and Method of Adjusting the Pacing Interval Thereof" and U.S. Pat. No. 4,944,298 (Sholder), entitled "Atrial Rate Based Programmable Pacemaker with Automatic Mode Switching Means". For a more detailed description of the various timing intervals used within the pacing device and their inter-relationship, see U.S. Pat. No. 4,788,980 (Mann et. al.), entitled "Pacemaker Having PVC Response and PMT Terminating Features". The '052, '555, '298 and '980 patents are incorporated herein by reference.

An atrial pulse generator 270 and a ventricular pulse generator 272 generate pacing stimulation pulses for delivery by the right atrial lead 120, the right ventricular lead 130, and/or the coronary sinus lead 124 via an electrode configuration switch 274. It is understood that in order to provide stimulation therapy in each of the four chambers of the heart, the atrial and ventricular pulse generators 270, 272 may include dedicated, independent pulse generators, multiplexed pulse generators, or shared pulse generators. The pulse generators 270, 272 are controlled by the microcontroller 260 via appropriate control signals 276, 278 respectively, to trigger or inhibit the stimulation pulses.

The microcontroller 260 further includes timing control circuitry 279 which is used to control pacing parameters (e.g., the timing of stimulation pulses) as well as to keep track of the timing of refractory periods, noise detection windows, evoked response windows, alert intervals, marker channel timing, etc., which is well known in the art. Examples of pacing parameters include, but are not limited to, atrio-ventricular delay, interventricular delay and interatrial delay.

The switch bank 274 includes a plurality of switches for connecting the desired electrodes to the appropriate I/O circuits, thereby providing complete electrode programmability. Accordingly, the switch 274, in response to a control signal 280 from the microcontroller 260, determines the polarity of the stimulation pulses (e.g., unipolar, bipolar, etc.) by selectively closing the appropriate combination of switches (not shown) as is known in the art.

Atrial sensing circuits 282 and ventricular sensing circuits 284 may also be selectively coupled to the right atrial lead 120, coronary sinus lead 124, and the right ventricular lead 130, through the switch 274 for detecting the presence of cardiac activity in each of the four chambers of the heart. Accordingly, the atrial and ventricular sensing circuits 282, 284 may include dedicated sense amplifiers, multiplexed amplifiers, or shared amplifiers. The switch 274 determines the "sensing polarity" of the cardiac signal by selectively closing the appropriate switches, as is also known in the art. In this way, the clinician may program the sensing polarity independent of the stimulation polarity.

Each sensing circuit 282, 284 preferably employs one or more low power, precision amplifiers with programmable gain and/or automatic gain control, bandpass filtering, and a threshold detection circuit, as known in the art, to selectively sense the cardiac signal of interest. The automatic gain control enables the device 110 to deal effectively with the difficult problem of sensing the low amplitude signal characteristics of atrial or ventricular fibrillation. Such sensing circuits 282, 284 can be used to determine cardiac performance values used in the present invention. Alternatively, an automatic sensitivity control circuit may be used to effectively deal with signals of varying amplitude.

The outputs of the atrial and ventricular sensing circuits 282, 284 are connected to the microcontroller 260 which, in turn, are able to trigger or inhibit the atrial and ventricular pulse generators 270, 272 respectively, in a demand fashion in response to the absence or presence of cardiac activity, in the appropriate chambers of the heart. The sensing circuits 282, 284 in turn, receive control signals over signal lines 286, 288 from the microcontroller 260 for purposes of measuring cardiac performance at appropriate times, and for controlling the gain, threshold, polarization charge removal circuitry (not shown), and timing of any blocking circuitry (not shown) coupled to the inputs of the sensing circuits 282, 286.

For arrhythmia detection and discrimination, the device 110 is shown as including an arrhythmia detector 262, a morphology detector 264, an atrial interval monitor 265 and a ventricular interval monitor 266, which can utilize the atrial and ventricular sensing circuits 282, 284 to sense cardiac signals to determine whether a rhythm is physiologic or pathologic. The morphology detector 264 can, e.g., assess characteristics such as amplitude, area under curves, polarity, and shape, of detected cardiac rhythms. The atrial interval monitor 265 and the ventricular interval monitor 266 can monitor atrial intervals and ventricular intervals from one or more EGMs, in order, e.g., to detect a sudden decrease in such intervals.

The arrhythmia detector 262 can analyze the timing intervals between sensed events (e.g., P-waves, R-waves, and depolarization signals associated with fibrillation) and compare them to predefined rate zone limits (e.g., bradycardia, normal, low rate VT, high rate VT, and fibrillation rate zones), and various other characteristics such as morphology (as determined by the morphology detector 264) and/or sudden onset, stability, physiologic sensors, etc., in order to classify an arrhythmia, and thus, determine the type of remedial therapy that is needed (e.g., bradycardia pacing, anti-tachycardia pacing, cardioversion shocks or defibrillation shocks).

The arrhythmia detector 262, morphology detector 264, atrial interval monitor 265 and ventricular interval monitor 266 can be implemented within the microcontroller 260, as shown in FIG. 2. Thus, the detectors/monitor 262, 264, 265 and/or 266 can be implemented by software, firmware, or combinations thereof. It is also possible that all, or portions, of the arrhythmia detector 262, morphology detector 264, atrial interval monitor 264 and/or ventricular interval monitor 266 can be implemented using hardware. Further, it is also possible that all, or portions, of the detectors/monitor 262, 264, 265 and/or 266 can be implemented separate from the microcontroller 260. It is also possible that the features of the arrhythmia detector, morphology detector, and atrial interval monitor 265 and ventricular interval monitor 266 can be incorporated into a single detector. The arrhythmia initiation discriminator 267 can receive information from an atrial interval monitor 265 and ventricular interval monitor 266. The information can be used the classifying an arrhythmia, as will be described in more detail below. The arrhythmia initiation discriminator 267 can be part of, or separate from, arrhythmia detector 262.

Exemplary types of arrhythmias that the arrhythmia detector 262 can detect include, but are not limited to, SVT (e.g., AF), VT and VF. A tachycardia is a fast heart rate (usually over 100 beats per minute) typically caused by disease or injury. It can also be part of a normal response to increased activity or oxygen demands. The average heart beats between 60 and 100 times per minute. When the tachycardia is due to disease or injury, it usually requires treatment. Tachycardias may begin in the upper chambers of the heart (the atria) or the lower chambers of the heart (the ventricles). VTs begin in the ventricles. Some are harmless, but others are life threatening in that they can quickly deteriorate to VF. Some VTs are harmful even before they deteriorate into VF, or even if they don't deteriorate to VF (e.g., they can cause hemodynamic deterioration that can cause collapse).

VF is a very fast (e.g., over 200 beats per minute) and chaotic heart rate in the lower chambers of the heart, resulting from multiple areas of the ventricles attempting to control the heart's rhythm. VF can occur spontaneously (generally caused by heart disease) or when VT has persisted too long. When the ventricles fibrillate, they do not contract normally, so they cannot effectively pump blood. The instant VF begins, effective blood pumping stops. VF typically quickly becomes more erratic, often resulting in sudden cardiac arrest. This arrhythmia should be corrected immediately via a shock from an external defibrillator or an implantable cardioverter defibrillator (ICD). The defibrillator stops the chaotic electrical activity and restores normal heart rhythm. These are just a few examples of the types of arrhythmias that the arrhythmia detector 262 can detect. One of ordinary skill in the art will appreciate that other types of arrhythmias can be detected, and information for such other types of arrhythmias can be stored.

In accordance with specific embodiments of the present invention, the implantable device 110 can store, in memory 294, IEGM signal data corresponding to the period immediately prior to, during and subsequent to a detected arrhythmia. The implantable device can also store data that identifies the type of arrhythmia, the time of the arrhythmia (e.g., a time stamp), the duration of the arrhythmia, as well as any other type of information that a caregiver may deem useful. U.S. Pat. No. 4,295,474 (Fischell), entitled "Recorder with Patient Alarm and Service Request Systems Suitable for use with Automatic Implantable Defibrillator" and U.S. Pat. No. 5,732,708 (Nau et al.), entitled "Method for Storing EGM and Diagnostic Data in a Read/Write Memory of an Implantable Cardiac Therapy Device" each of which is incorporated herein by reference, provide exemplary additional details of the types of data that can be stored in response to the detection of an arrhythmia (and other cardiac events), and how such data can be efficiently and effectively stored.

Still referring to FIG. 2, cardiac signals are also applied to the inputs of an analog-to-digital (A/D) data acquisition system 290. The data acquisition system 290 is configured to acquire intracardiac electrogram (IEGM) signals, convert the raw analog data into a digital signal, and store the digital signals for later processing and/or telemetric transmission to an external device 202. The data acquisition system 290 is coupled to the right atrial lead 120, the coronary sinus lead 124, and the right ventricular lead 130, and/or any other lead, through the switch 274 to sample cardiac signals across any pair of desired electrodes. In specific embodiments, the data acquisition system 290 may be used to acquire IEGM signals for the analysis.

In accordance with specific embodiments of the present invention, the memory 294 includes a buffer 295 that continually stores a portion of an acquired IEGM signal, e.g., that last 30 seconds, last minute, last 5 minutes, etc. of a wideband IEGM signal. Alternatively, such a buffer can be part of the on-chip memory of the controller 260. It's also possible that there be a buffer dedicated to storing a recent portion of an IEGM signal. Such a dedicated buffer can be receive, e.g., the output of the data acquisition system 290. In accordance with specific embodiments of the present invention, such a buffer, regardless of where it is located, enables the implantable system to analyze a portion of an IEGM signal that leads up to the onset of a tachycardia, as will be described in further detail below. Alternatively, atrial and/or ventricular interval metrics can be determined in real or near real time and such metrics can be stored in the buffer.

The data acquisition system 290 can be coupled to the microcontroller 260, or other detection circuitry, for detecting an evoked response from the heart 112 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 260 detects a depolarization signal during a window following a stimulation pulse, the presence of which indicates that capture has occurred. The microcontroller 260 enables capture detection by triggering the ventricular pulse generator 272 to generate a stimulation pulse, starting a capture detection window using the timing control circuitry 279 within the microcontroller 260, and enabling the data acquisition system 290 via control signal 292 to sample the cardiac signal that falls in the capture detection window and, based on the amplitude, determines if capture has occurred.

The implementation of capture detection circuitry and algorithms are well known. See for example, U.S. Pat. No. 4,729,376 (Decote, Jr.), entitled "Cardiac Pacer and Method Providing Means for Periodically Determining Capture Threshold and Adjusting Pulse Output Level Accordingly"; U.S. Pat. No. 4,708,142 (Decote, Jr.), entitled "Automatic Cardiac Capture Threshold Determination System and Method"; U.S. Pat. No. 4,686,988 (Sholder), entitled "Pacemaker System and Method for Measuring and Monitoring Cardiac Activity and for Determining and Maintaining Capture"; U.S. Pat. No. 4,969,467 (Callaghan et. al.), entitled "Pacemaker with Improved Automatic Output Regulation"; and U.S. Pat. No. 5,350,410 (Kleks et. al.), entitled "Autocapture System for Implantable Pulse Generator", which patents are hereby incorporated herein by reference. The type of capture detection system used is not critical to the present invention.

The microcontroller 260 is further coupled to the memory 294 by a suitable data/address bus 296, wherein the programmable operating parameters used by the microcontroller 260 are stored and modified, as required, in order to customize the operation of the implantable device 110 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 112 within each respective tier of therapy.

The operating parameters of the implantable device 110, including arrhythmia discrimination parameters and algorithms, may be non-invasively programmed into the memory 294 through a telemetry circuit 201 in telemetric communication with an external device 202, such as a programmer, transtelephonic transceiver, or a diagnostic system analyzer. The telemetry circuit 201 can be activated by the microcontroller 260 by a control signal 206. The telemetry circuit 201 advantageously allows intracardiac electrograms and status information relating to the operation of the device 110 (as contained in the microcontroller 260 or memory 294) to be sent to the external device 202 through an established communication link 205. For examples of such devices, see U.S. Pat. No. 4,809,697, entitled "Interactive Programming and Diagnostic System for use with Implantable Pacemaker" (Causey, III et al.); U.S. Pat. No. 4,944,299, entitled "High Speed Digital Telemetry System for Implantable Device" (Silvian); and U.S. Pat. No. 6,275,734 entitled "Efficient Generation of Sensing Signals in an Implantable Medical Device such as a Pacemaker or ICD" (McClure et al.), which patents are hereby incorporated herein by reference.

The implantable device 110 additionally includes a battery 211 which provides operating power to all of the circuits shown in FIG. 2. If the implantable device 110 also employs shocking therapy, the battery 211 should be capable of operating at low current drains for long periods of time, and then be capable of providing high-current pulses (for capacitor charging) when the patient requires a shock pulse. The battery 211 should also have a predictable discharge characteristic so that elective replacement time can be detected. Certain embodiments of the present invention, as will be appreciated from the discussion further below, can be used to extend the life a the battery 211 by reducing the quantity of high voltage shocks delivered.

The implantable device 110 can also include a magnet detection circuitry (not shown), coupled to the microcontroller 260. It is the purpose of the magnet detection circuitry to detect when a magnet is placed over the implantable device 110, which magnet may be used by a clinician to perform various test functions of the implantable device 110 and/or to signal the microcontroller 260 that the external programmer 202 is in place to receive or transmit data to the microcontroller 260 through the telemetry circuits 201.

As further shown in FIG. 2, the device 110 is also shown as having an impedance measuring circuit 213 which is enabled by the microcontroller 260 via a control signal 214. The known uses for an impedance measuring circuit 213 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds and heart failure condition; detecting when the device has been implanted; measuring stroke volume; and detecting the opening of heart valves, etc. The impedance measuring circuit 213 is advantageously coupled to the switch 274 so that any desired electrode may be used. The impedance measuring circuit 213 is not critical to the present invention and is shown only for completeness.

Because the implantable device 110 may operate as an implantable cardioverter defibrillator device, it should detect the occurrence of an arrhythmia, and automatically apply an appropriate electrical shock therapy to the heart aimed at terminating the detected arrhythmia. To this end, the microcontroller 260 further controls a shocking circuit 216 by way of a control signal 218. The shocking circuit 216 generates shocking pulses of low (up to 0.5 Joules), moderate (0.5-10 Joules), or high energy (11 to 40 Joules), as controlled by the microcontroller 260. Such shocking pulses are applied to the patient's heart 112 through at least two shocking electrodes, e.g., selected from the left atrial coil electrode 128, the RV coil electrode 136, and/or the SVC coil electrode 138. As noted above, the housing 240 may act as an active electrode in combination with the RV electrode 136, or as part of a split electrical vector using the SVC coil electrode 138 or the left atrial coil electrode 128 (i.e., using the RV electrode as a common electrode). Use of additional and/or alternative electrodes is also possible, as would be appreciated by one of ordinary skill in the art.

The above described implantable device 110 was described as an exemplary device. One or ordinary skill in the art would understand that embodiments of the present invention can be used with alternative types of implantable devices. Accordingly, embodiments of the present invention should not be limited to use only with the above described device.

Figure 3:
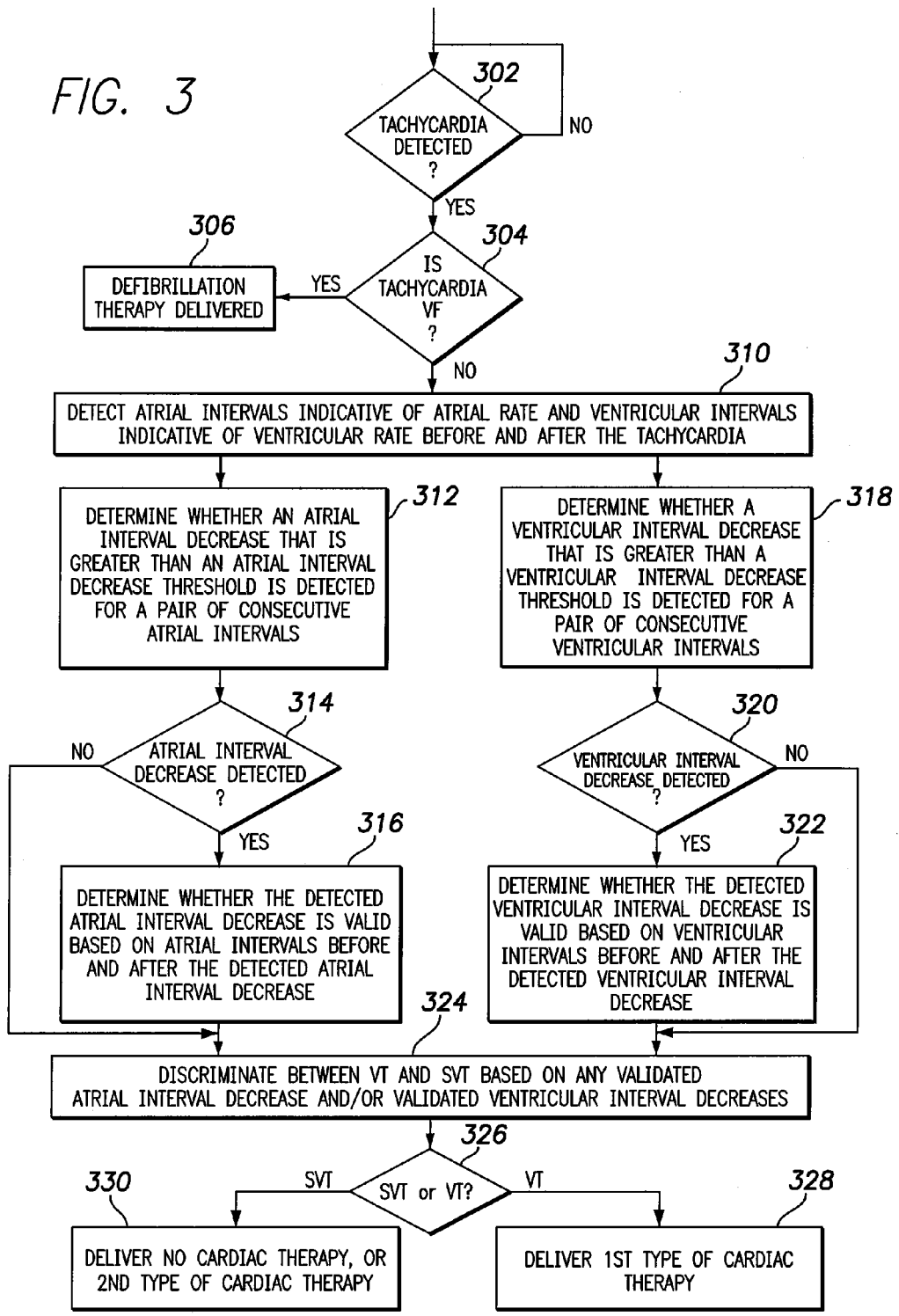
FIG. 3 is a high level flow diagram that is used to summarize specific embodiments of the present invention that relate to discriminating between VT and SVT.
Figure 4:
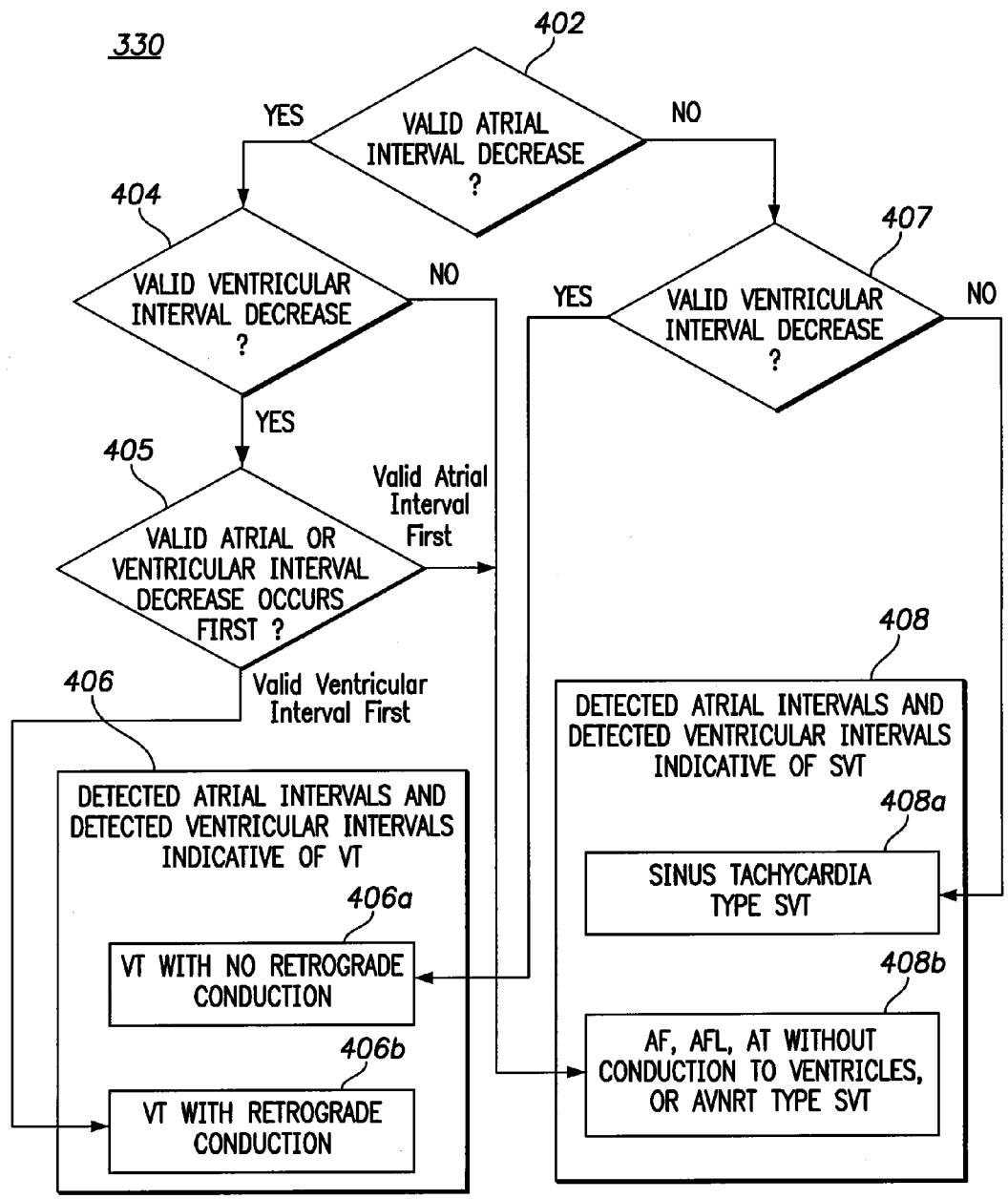
FIG. 4 is a high level flow diagram that is used to provide additional details of one of the steps of FIG. 3, according to an embodiment of the present invention, which relates to discriminating between VT and SVT based on any validated atrial interval decrease and/or validated ventricular interval decrease.

Specific embodiments of the present invention shall now be summarized with reference to the high level flow diagrams of FIGS. 3 and 4. Such embodiments can be used with an implantable cardiac device that discriminates between VT and SVT, such as but not limited to the device 110.

Referring to the top of FIG. 3, monitoring for a tachycardia occurs at step 302. This can include obtaining one or more intracardiac electrogram (IEGM) signals, so that the IEGM signal(s) can be monitored to detect tachycardias. Exemplary leads and electrodes that can be used to obtain an IEGM were discussed above with reference to FIGS. 1 and 2. It is well know how to obtain an IEGM, thus additional details of how to obtain an IEGM are not necessary.

As mentioned above, a tachycardia is any cardiac arrhythmia characterized by a rapid rate, e.g., usually over 100 beats per minute (BPM). Tachycardias may be normal, as in the case of a sinus tachycardia induced by exercise, or may indicate an abnormal rhythm, e.g., VT or VF. A tachycardia can be monitored for by monitoring ventricular and/or atrial cycle lengths and/or rates, and comparing such metric(s) to an appropriate threshold(s). For example, a tachycardia can be detected if a ventricular cycle length (CL) falls below a VT CL threshold or a ventricular rate exceeds a VT rate threshold. Other tachycardia detection techniques are also possible, and within the scope of the present invention.

Step 302 is repeated until a tachycardia is detected. When a tachycardia is detected, there can be an immediate discrimination between VT and SVT, or preferably, there is first a determination of whether the tachycardia is VF, as shown at step 304. VF detection can occur, e.g., when the ventricular rate is determined to exceed a VF rate threshold. Other VF detection techniques are also possible, and within the scope of the present invention. If VF is diagnosed, then defibrillation therapy can be delivered, as indicated at step 306, in an attempt to convert the VF to a normal sinus rhythm. Defibrillation therapy can include, e.g., delivery of defibrillation shocks, but is not limited thereto.

If it is determined at step 304 that the tachycardia is not VF, then steps 310-330 are performed to determine whether the tachycardia is either VT or SVT. In other words, arrhythmia discrimination takes place, details of which are explained below.

At step 310, there is a detection of atrial and ventricular intervals indicative of atrial and ventricular rate before and after the tachycardia. The atrial and ventricular intervals are times between particular features of atrial or ventricular cardiac signals. The features can be derived or otherwise detected, e.g., from an IEGM. Separate atrial EGM (AEGM) and ventricular EGM (VEGM) signals can be obtained, or respective atrial and ventricular features used to determine the atrial and ventricular intervals can be identified from a single IEGM signal that includes features indicative of both atrial and ventricular activity.

The atrial and ventricular interval values can be stored for a sliding window of time. In an embodiment, the window of time can be a fixed period of time, e.g. 8 seconds before an arrhythmia and 4 seconds after an arrhythmia.

At steps 312 and 314, there is a determination of whether there is an atrial interval decrease between a pair of consecutive atrial intervals that is greater than an atrial interval decrease threshold. In one embodiment, the atrial interval decrease threshold is 40 ms. Other atrial interval decreasing thresholds are possible, and with the scope of the present invention.

If an atrial interval decrease is detected, and then at step 316 it is determined whether the atrial interval decrease is valid based on atrial intervals before and after the detected atrial interval decrease. Step 316 is performed so as to distinguish a temporary transient decrease in an atrial interval (which quickly returns to its previous interval) from a sustained decrease in an atrial interval which may be indicative of an actual arrhythmia. Step 316 will also distinguish an atrial interval decrease that is detected due to noise or some other anomaly from an actual sustained decrease in an atrial interval. In accordance with an embodiment, step 316 is performed by comparing a certain number of atrial intervals before the atrial interval decrease to a preceding atrial interval threshold, and comparing certain number of atrial intervals after the atrial interval decrease threshold to a succeeding atrial interval threshold. If a predetermined number (e.g. 5) of atrial intervals before the detected atrial interval decrease are each greater than the preceding atrial interval threshold, and a predetermined number (e.g. 5) of atrial intervals after the detected atrial interval decrease are each less than the succeeding atrial interval threshold, then the detected atrial interval is validated. In an alternative embodiment, if at least N of M (e.g., 4 of 5) atrial intervals before the detected atrial interval decrease are each greater than the preceding atrial interval threshold, and at least X of Y (e.g., 4 of 5) atrial intervals after the detected atrial interval decrease are each less than the succeeding atrial interval threshold, then the detected atrial interval decrease is validated.

At steps 318 and 320, there is a determination of whether there is a ventricular interval decrease between a pair of consecutive ventricular intervals that is greater than an interval decrease threshold. In one embodiment, the ventricular interval decrease threshold is 40 ms. Other ventricular interval decrease thresholds are possible and within the scope of this invention. If such a ventricular interval decrease is detected, then at step 322 it is determined whether the ventricular intervals decrease is valid based on ventricular intervals before and after the detected ventricular interval decrease. The techniques for validating a detected ventricular interval decrease at step 322 are similar to the techniques for validating a detected atrial interval decrease at step 316, and thus need not be describe again in detail.

At step 324, discrimination between VT and SVT is performed based on any validated atrial interval decrease and/or validated ventricular interval decrease. As will be appreciated from the discussion below, the phrase "based on", unless stated otherwise, means based at least in part on, meaning that when a determination is "based on" a factor, other factors can also be used in making the determination. Exemplary details of such a discrimination are described below with respect to FIG. 4.

As shown as steps 326, 328 and 330, based on whether the tachycardia is classified as VT or SVT, different types of cardiac therapy can be delivered. If the tachycardia is classified as VT, then a first type of cardiac therapy can be delivered, as shown at step 328. The first type of cardiac therapy can include ventricular anti-tachycardia pacing (ATP) and/or cardioversion shocks, but is not limited thereto. If the tachycardia is classified as SVT, then a second type of cardiac therapy, or no cardiac therapy, can be delivered, as shown at step 330. The second type of cardiac therapy can include, e.g., atrial ATP or atrial defibrillation.

FIG. 4 will now be used to explain additional details of step 324, which involves discriminating between VT and SVT based on a validated atrial interval decrease and/or a validated ventricular interval decrease. Referring to FIG. 4, if it is determined at step 402 that there is a valid atrial interval decrease, and there is no valid ventricular interval decrease (as determined at step 404), then this is indicative of AF, AFL, AT without conduction to ventricles, or atrioventricular nodal reentry tachycardia (AVNRT), which are types of SVT, as indicated by the arrow from step 404 to block 408b.

If it is determined at step 402 that there is a valid atrial interval decrease, and it is determined at step 404 that there is also a valid ventricular interval decrease, then it is determined at step 405 whether the valid atrial interval decrease or the valid ventricular interval decrease occurred first. If the valid ventricular interval decrease occurs before the valid atrial interval decrease, then this is indicative of VT with retrograde conduction, as indicated from the arrow from step 405 to block 406b. However, if the valid atrial interval decrease occurs before the valid ventricular interval, then this is also indicative of AF, AFL, AT without conduction to ventricles, or AVNRT, which are types of SVT, as indicated by the arrow from step 405 to block 408b.

If it determined at step 402 that there is no valid atrial interval decrease, but at step 407 it is determined that there is a valid ventricular interval decrease, then this is indicative of VT with no retrograde conduction, as indicated by the arrow from step 407 to block 406a.

If it is determined at step 402 that there is no valid atrial interval decrease, and it is determined at step 407 that there is no valid ventricular interval decrease, then this is indicative of sinus tachycardia type SVT, as indicated by the arrow from step 407 to block 408a.

Figure 5A:
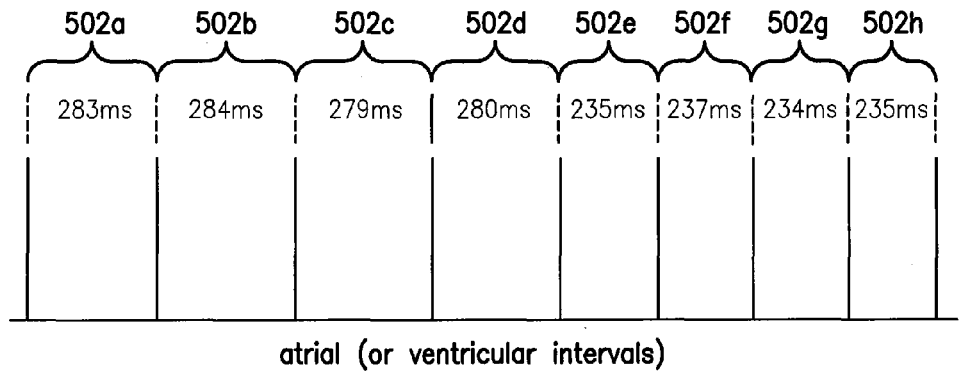
FIGS. 5A and 5B are exemplary diagrams that are useful for explaining how a detected atrial or ventricular interval decrease can be validated in accordance with an embodiment.
Figure 5B:
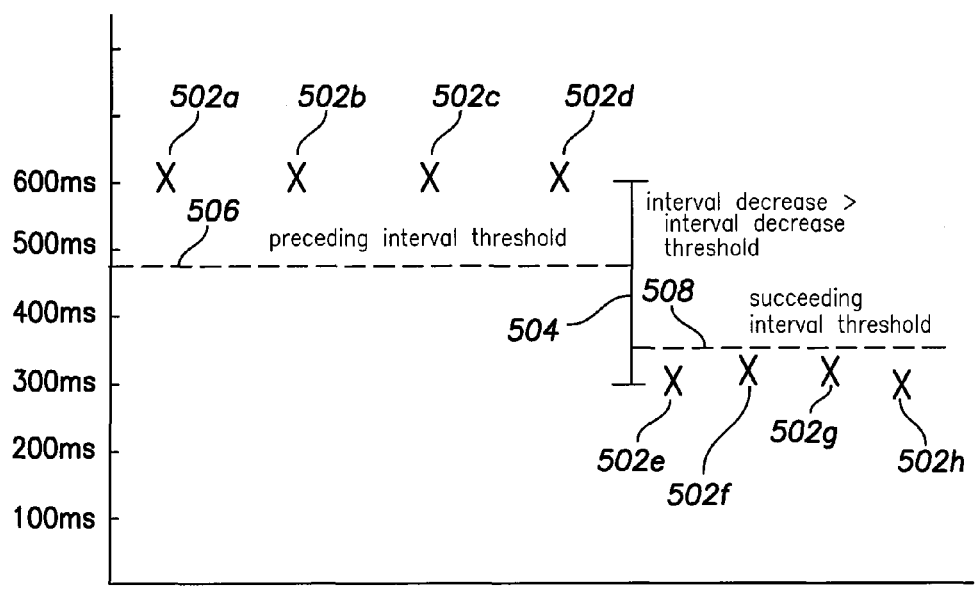

FIGS. 5A and 5B are exemplary diagrams that are useful for explaining how a detected atrial or ventricular interval decrease can be validated in accordance with an embodiment. The intervals represented in these figures can represent atrial or ventricular intervals. FIG. 5A shows a number of consecutive intervals 502a-h. These intervals 502a-h are also graphed in FIG. 5B. In order to detect an atrial interval decrease (or a ventricular interval decrease), intervals can be checked until one consecutive pair has a decrease greater than an interval decrease threshold (e.g., 40 ms). In this example, the interval decrease 504 between interval 502*d* and interval 502*e* is greater than the interval decrease threshold. As was explained above with reference to steps 314 and 316 (and 320 and 322), once an atrial (or ventricular) interval decrease is detected, there is a determination of whether the detected interval decrease is valid based on intervals before and after the detected atrial (or ventricular) interval decrease. As was explained above, this can be performed by comparing a certain number of atrial (or ventricular) intervals before the atrial (or ventricular) interval decrease to a preceding atrial (or ventricular) interval threshold, and comparing certain number of atrial (or ventricular) intervals after the atrial (or ventricular) interval decrease threshold to a succeeding atrial (or ventricular) interval threshold. In accordance with an embodiment, the preceding interval threshold 506 can be calculated using the value of the first interval in the pair of intervals for the interval decrease being validated, in this case interval 502*d*. For example, the preceding interval threshold 506 can be set at 80%, or some other percentage, of the interval 502*d*. In this case, each of the intervals 502*a-c* before the interval decrease is greater than the preceding interval threshold 506. The succeeding interval threshold 508 can be calculated using the value of the second interval in the pair of intervals for the interval decrease being validated, in this case interval 502*e*. For example, the succeeding interval threshold 508 can be set at 120%, or some other percentage, of the interval 502*e*. In this case, each of the intervals 502*f-h* after the interval decrease is less than the succeeding interval threshold 508.

Alternately, the preceding interval threshold 506 and succeeding interval threshold 508 can be determined in some other fashion, while still being within the scope of an embodiment of the present invention. For example, these thresholds can be some other function of one or more of the pair of intervals associated with the interval decrease being validated.

The above described arrhythmia initiation analysis can be used as the sole arrhythmia discrimination qualifier, are more likely, as one of a few or many discrimination qualifiers, some of which were discussed above, including morphology, sudden onset, and interval stability (also known as rate stability). In other words, the above described arrhythmia initiation analysis can be used to independently discriminate between VT and SVT, or can be used together with other techniques for discrimination between VT and SVT. For example, the above described embodiments can be used to supplement (e.g., to increase the confidence level of) arrhythmia discrimination performed using some other technique(s), including but not limited to interval stability, sudden onset and morphology discrimination techniques. Alternatively, some other technique(s) can be used to supplement the arrhythmia discrimination performed using the arrhythmia initiation analysis described above. It is also possible that the arrhythmia initiation analysis be used in one or more branch of rate branch algorithm, examples of which are described below. Some exemplary details of interval stability, sudden onset and morphology discrimination techniques are provided below, for completeness.

Interval stability discrimination techniques can be used to assist in discriminating between episodes of VT and episodes of AF (which is a type of SVT), because VTs are typically very stable, whereas the rhythm from one beat to the next during AF is typically less stable (i.e., more irregular). Depending upon the algorithm used, the value of an interval stability parameter can be a value of stability (also referred to as variability), which can be defined by a range, variance, standard deviation, or the like. For example, if a cardiac rhythm exceeds the tachycardia detection rate parameter, and the stability is within that defined by the stability discriminator value (e.g., the standard deviation of the rhythm is less than the standard deviation discriminator value), and then the implantable cardiac device can interpret that as an indicator of VT. Interval stability is sometime referred to as rate stability, because rate and interval are simply inverses of one another.

Sudden onset discrimination techniques can be used to assist in distinguishing between VT and a sinus tachycardia type SVT that is due to exercise (e.g., walking up a flight of stairs). Typically, a sinus tachycardia has a gradual rate of onset, while VT has a more abrupt onset. Such onset can be measured, e.g., by determining a difference between the average RR interval for N beats prior to a first beat that exceeds the tachycardia detection rate, and the average RR interval for N beats following the first beat that exceeds the tachycardia detection rate (e.g., N can be 1 or more). Accordingly, the value of a sudden onset discriminator parameter can be specified in milliseconds. Where the sudden onset discriminator value is exceeded, the implantable cardiac device interprets that as an indicator of VT. Where a sudden onset discriminator value is not exceeded, the implantable cardiac device interprets that as an indicator of SVT.

Morphology discrimination techniques can be also be used to assist in discrimination between VT and SVT, because SVTs originate in the atria and follow the normal conduction pathway to the ventricles (typically via the AV node), causing the morphology (shape) of the resulting QRS complexes to look similar to the morphology of a QRS complex of a normal sinus rhythm. In contrast, VT arises from outside normal conduction system, causing the morphology of the resulting QRS complex to be less similar to that of a normal sinus rhythm. To perform such morphology comparisons, a template QRS complex is typically obtained and stored when a patient is known to have a normal sinus rhythm. Thereafter, the template QRS complex can be compared to present QRS complexes in real or near real time, to determine a level of similarity. A morphology discriminator parameter can specify, e.g., the level of similarity below which a rhythm is classified as indicative of VT, and above which the rhythm is classified as indicative of SVT. For a more specific example, a morphology algorithm can measure attributes such as the number of peaks, amplitude of peaks, polarity, and area under curves of a QRS complex, and compares such complexes to the template QRS complex to generate a percent match between 0 and 100%. For this example, a morphology discriminator parameter can specify the percentage match, above which the implantable cardiac device interprets as indicative of SVT, and below which the device interprets as indicative of VT.

In accordance with specific embodiments, the implantable systems can substantially continually monitoring for a tachycardia, and substantially continually monitoring for valid atrial and ventricular interval decreases while monitoring for a tachycardia. This way, when a tachycardia is detected, there can be a substantially immediate analysis of any valid atrial and/or ventricular interval decreased as discussed above.

In an alternative embodiment, the detection of a tachycardia by the implantable system can trigger the analysis of atrial and ventricular interval decreases. More specifically, a portion of an IEGM signal or signals can be repeatedly stored in a buffer (e.g., buffer 295). Then, a fixed time after a tachycardia is detected, the contents of the buffer can be froze, so that the contents of the buffer includes a portion of the IEGM signal or signals indicative of cardiac activity before and after the detected tachycardia. The implantable system can then determine, based on the contents of the buffer, the valid atrial and ventricular interval deceases.

In one rate branch algorithm, the present arrhythmia initiation analysis and conventional methods like morphology and interval stability can be independently used to discriminate between VT and SVT. The final discrimination between VT and SVT can be based on a majority of the independent determinations. Alternatively, arrhythmia initiation method can be performed as a sub-branch of a sudden onset algorithm or other method.

In one exemplary method, when V<A, interval stability, morphology and the present arrhythmia initiation methods are independently performed with results of the best two out of three independent methods indicating VT or SVT.

If V=A, the arrhythmia detection method can be performed when an atrioventricular interval (AVI) analysis, which may analyze, e.g., PR intervals, indicates that the AVI is indicative of SVT. The present arrhythmia initiation method can then be performed in parallel with a morphology method, or in parallel with morphology and sudden onset methods.

The arrhythmia initiation analysis can be performed in response to detecting a tachycardia, in response to detecting a tachycardia where the ventricular rate exceeds a VT threshold but does not exceed a ventricular fibrillation (VF) threshold, or in response to detecting a tachycardia where the ventricular rate is less than or substantially equal to the atrial rate.

The present invention has been described above with the aid of functional building blocks illustrating the performance of specified functions and relationships thereof. The boundaries of these functional building blocks have often been arbitrarily defined herein for the convenience of the description. Alternate boundaries can be defined so long as the specified functions and relationships thereof are appropriately performed. Any such alternate boundaries are thus within the scope and spirit of the claimed invention. For example, it would be possible to combine or separate some of the steps shown in FIGS. without substantially changing the overall events and results.

The previous description of the preferred embodiments is provided to enable any person skilled in the art to make or use the embodiments of the present invention. While the invention has been particularly shown and described with reference to preferred embodiments thereof, it will be understood by those skilled in the art that various changes in form and details may be made therein without departing from the spirit and scope of the invention.

What is claimed is:

1. For use by an implantable system, a method for discriminating between ventricular tachycardia (VT) and supraventricular tachycardia (SVT), comprising:
   (a) detecting atrial intervals indicative of atrial rate and ventricular intervals indicative of ventricular rate within a window leading up to and following the onset of a tachycardia;
   (b) determining whether a valid atrial interval decrease is detected within the window by
      (b.1) determining whether an atrial interval decrease that is greater than an atrial interval decrease threshold is detected for a pair of consecutive atrial intervals within the window, and
      (b.2) if the atrial interval decrease is detected, determining whether the detected atrial interval decrease is valid based on atrial intervals before and after the detected atrial interval decrease;
   (c) determining whether a valid ventricular interval decrease is detected within the window by
      (c.1) determining whether a ventricular interval decrease that is greater than a ventricular interval decrease threshold is detected for a pair of consecutive ventricular intervals within the window, and
      (c.2) if the ventricular interval decrease is detected, determining whether the detected ventricular interval decrease is valid based on ventricular intervals before and after the detected ventricular interval decrease; and
   (d) discriminating between VT and SVT based on results of step (b) and (c);
   wherein step (d) comprises determining that the detected atrial intervals and the detected ventricular intervals within the window are indicative of SVT if both a valid atrial interval decrease is detected and a valid ventricular interval decrease is detected within the window, and the valid atrial interval change occurs prior to the valid ventricular interval change.

2. The method of claim 1, wherein:
step (b.2) comprises determining that the detected atrial interval decrease is valid if a predetermined number of atrial intervals before the detected atrial interval decrease are each greater than a preceding atrial interval threshold, and a predetermined number of atrial intervals after the detected atrial interval decrease are each less than a succeeding atrial interval threshold; and
step (c.2) comprises determining that the detected ventricular interval decrease is valid if a predetermined number of ventricular intervals before the detected ventricular interval decrease are each greater than a preceding ventricular interval threshold, and a predetermined number of ventricular intervals after the detected ventricular interval decrease are each less than a succeeding ventricular interval threshold.

3. The method of claim 2, wherein:
step (b.2) comprises determining that the detected atrial interval decrease is valid if at least N of M atrial intervals before the detected atrial interval decrease are each greater than the preceding atrial interval threshold, and at least X of Y atrial intervals after the detected atrial interval decrease are each less than the succeeding atrial interval threshold; and
step (c.2) comprises determining that the detected ventricular interval decrease is valid if at least N of M ventricular intervals before the detected ventricular interval decrease are each greater than the preceding ventricular interval threshold, and at least X of Y ventricular intervals after the detected ventricular interval decrease are each less than the succeeding ventricular interval threshold.

4. The method of claim 1, wherein:
step (d) comprises determining that the detected atrial intervals and the detected ventricular intervals within the window are indicative of SVT if no valid atrial interval decrease is detected and no valid ventricular interval decrease is detected within the window.

5. The method of claim 1, wherein:
step (d) comprises determining that the detected atrial intervals and the detected ventricular intervals within the window are indicative of SVT if a valid atrial interval decrease is detected and no valid ventricular interval decrease is detected within the window.

6. The method of claim 1, wherein:
step (d) comprises determining that the detected atrial intervals and the detected ventricular intervals within the window are indicative of VT if no valid atrial interval decrease is detected and a valid ventricular interval decrease is detected within the window.

7. The method of claim 1, wherein step (d) comprises:
   (d.1) determining that the detected atrial intervals and the detected ventricular intervals within the window are indicative of SVT if
      (d.1.a) no valid atrial interval decrease is detected and no valid ventricular interval decrease is detected within the window,
      (d.1.b) a valid atrial interval decrease is detected and no valid ventricular interval decrease is detected within the window, or
      (d.1.c) both a valid atrial interval decrease is detected and a valid ventricular interval decrease is detected within the window, and the valid atrial interval change occurs prior to the valid ventricular interval change; and
   (d.2) determining that the detected atrial intervals and the detected ventricular intervals within the window are indicative of VT if
      (d.2.a) no valid atrial interval decrease is detected and a valid ventricular interval decrease is detected within the window, or
      (d.2.b) both a valid atrial interval decrease is detected and a valid ventricular interval decrease is detected within the window, and the valid ventricular interval change occurs prior to the valid atrial interval change.

8. The method of claim 1, further comprising:
   (e) providing a first type of cardiac therapy if it is determined at step (d) that the detected tachycardia is VT; and
   (f) providing a second type of cardiac therapy if it is determined at step (d) that the detected tachycardia is SVT.

9. The method of claim 1, further comprising monitoring for a tachycardia, and performing steps (a), (b), (c) and (d) in response to detecting a tachycardia.

10. The method of claim 1, further comprising monitoring for a tachycardia, and performing steps (a), (b), (c) and (d) in response to detecting a tachycardia where the ventricular rate exceeds a VT threshold but does not exceed a ventricular fibrillation (VF) threshold.

11. The method of claim 1, further comprising monitoring for a tachycardia, and performing steps (a), (b), (c) and (d) in response to detecting a tachycardia where the ventricular rate is less than or substantially equal to the atrial rate.

12. For use by an implantable system, a method for discriminating between ventricular tachycardia (VT) and supraventricular tachycardia (SVT), comprising:
   (a) detecting atrial intervals indicative of atrial rate and ventricular intervals indicative of ventricular rate within a window leading up to and following the onset of a tachycardia;
   (b) determining whether a valid atrial interval decrease is detected within the window by
      (b.1) determining whether an atrial interval decrease that is greater than an atrial interval decrease threshold is detected for a pair of consecutive atrial intervals within the window, and
      (b.2) if the atrial interval decrease is detected, determining whether the detected atrial interval decrease is valid based on atrial intervals before and after the detected atrial interval decrease;
   (c) determining whether a valid ventricular interval decrease is detected within the window by
      (c.1) determining whether a ventricular interval decrease that is greater than a ventricular interval decrease threshold is detected for a pair of consecutive ventricular intervals within the window, and
      (c.2) if the ventricular interval decrease is detected, determining whether the detected ventricular interval decrease is valid based on ventricular intervals before and after the detected ventricular interval decrease; and
   (d) discriminating between VT and SVT based on results of step (b) and (c);
   wherein step (d) comprises determining that the detected atrial intervals and the detected ventricular intervals within the window are indicative of VT if both a valid atrial interval decrease is detected and a valid ventricular interval decrease is detected within the window, and the valid ventricular interval change occurs prior to the valid atrial interval change.

13. An implantable system capable of discriminating between ventricular tachycardia (VT) and supraventricular tachycardia (SVT), comprising:
   a monitor configured to detect atrial intervals indicative of atrial rate and ventricular intervals indicative of ventricular rate within a window leading up to and following the onset of a tachycardia; and
   an arrhythmia discriminator configured to:
   determine whether a valid atrial interval decrease is detected within the window by determining whether an atrial interval decrease that is greater than an atrial interval decrease threshold is detected for a pair of consecutive atrial intervals within the window,
   if the atrial interval decrease is detected, determine whether the detected atrial interval decrease is valid based on atrial intervals before and after the detected atrial interval decrease,
   determine whether a valid ventricular interval decrease is detected within the window by determining whether a ventricular interval decrease that is greater than a ventricular interval decrease threshold is detected for a pair of consecutive ventricular intervals within the window,
   if the ventricular interval decrease is detected, determine whether the detected ventricular interval decrease is valid based on ventricular intervals before and after the detected ventricular interval decrease, and
   discriminate between VT and SVT based on the determinations;
   wherein the arrhythmia detector is configured to determine that the detected atrial intervals and the detected ventricular intervals within the window are indicative of SVT if both a valid atrial interval decrease is detected and a valid ventricular interval decrease is detected within the window, and the valid atrial interval change occurs prior to the valid ventricular interval change.

14. An implantable system capable of discriminating between ventricular tachycardia (VT) and supraventricular tachycardia (SVT), comprising:
   a monitor configured to detect atrial intervals indicative of atrial rate and ventricular intervals indicative of ventricular rate within a window leading up to and following the onset of a tachycardia; and
   an arrhythmia discriminator configured to:
   determine whether a valid atrial interval decrease is detected within the window by determining whether an atrial interval decrease that is greater than an atrial interval decrease threshold is detected for a pair of consecutive atrial intervals within the window, if the atrial interval decrease is detected, determine whether the detected atrial interval decrease is valid based on atrial intervals before and after the detected atrial interval decrease, determine whether a valid ventricular interval decrease is detected within the window by determining whether a ventricular interval decrease that is greater than a ventricular interval decrease threshold is detected for a pair of consecutive ventricular intervals within the window, if the ventricular interval decrease is detected, determine whether the detected ventricular interval decrease is valid based on ventricular intervals before and after the detected ventricular interval decrease, and discriminate between VT and SVT based on the determinations;

wherein the arrhythmia detector is configured to determine that the detected atrial intervals and the detected ventricular intervals within the window are indicative of VT if both a valid atrial interval decrease is detected and a valid ventricular interval decrease is detected within the window, and the valid ventricular interval change occurs prior to the valid atrial interval change.

15. The implantable system of claim 14, wherein:

the arrhythmia detector is configured to determine that the detected atrial interval decrease is valid if a predetermined number of atrial intervals before the detected atrial interval decrease are each greater than a preceding atrial interval threshold, and a predetermined number of atrial intervals after the detected atrial interval decrease are each less than a succeeding atrial interval threshold; and the arrhythmia detector is configured to determine that the detected ventricular interval decrease is valid if a predetermined number of ventricular intervals before the detected ventricular interval decrease are each greater than a preceding ventricular interval threshold, and a predetermined number of ventricular intervals after the detected ventricular interval decrease are each less than a succeeding ventricular interval threshold.

16. The implantable system of claim 1, wherein:

the arrhythmia detector is configured to determine that the detected atrial interval decrease is valid if at least N of M atrial intervals before the detected atrial interval decrease are each greater than the preceding atrial interval threshold, and at least X of Y atrial intervals after the detected atrial interval decrease are each less than the succeeding atrial interval threshold; and the arrhythmia detector is configured to determine that the detected ventricular interval decrease is valid if at least N of M ventricular intervals before the detected ventricular interval decrease are each greater than the preceding ventricular interval threshold, and at least X of Y predetermined number of ventricular intervals after the detected ventricular interval decrease are each less than the succeeding ventricular interval threshold.

17. The implantable system of claim 14, wherein:

the arrhythmia detector is configured to determine that the detected atrial intervals and the detected ventricular intervals within the window are indicative of SVT if no valid atrial interval decrease is detected and no valid ventricular interval decrease is detected within the window.

18. The implantable system of claim 14, wherein:

the arrhythmia detector is configured to determine that the detected atrial intervals and the detected ventricular intervals within the window are indicative of SVT if a valid atrial interval decrease is detected and no valid ventricular interval decrease is detected within the window.

19. The implantable system of claim 14, wherein:

the arrhythmia detector is configured to determine that the detected atrial intervals and the detected ventricular intervals within the window are indicative of VT if no valid atrial interval decrease is detected and a valid ventricular interval decrease is detected within the window.

20. The implantable system of claim 14, wherein:

the arrhythmia detector is configured to discriminate between VT and SVT based on the determination and additional criteria.

21. The implantable system of claim 14, wherein the implantable system provides a first type of cardiac therapy if it is determined that the detected tachycardia is VT; and provides a second type of cardiac therapy if it is determined that the detected tachycardia is SVT.

* * * * *